United States Patent [19]
Townsend et al.

[11] Patent Number: 5,514,593
[45] Date of Patent: May 7, 1996

[54] TIME AVERAGED TOXIC METALS MONITORING METHOD

[75] Inventors: Carl W. Townsend, Lost Angeles; John McHardy, Westlake Village; Clifford A. Megerle, Thousand Oaks, all of Calif.

[73] Assignee: Hughes Aircraft Company, Los Angeles, Calif.

[21] Appl. No.: 283,344

[22] Filed: Aug. 1, 1994

[51] Int. Cl.$^6$ ............................ G01N 33/20; G01N 21/78
[52] U.S. Cl. ..................... 436/77; 436/52; 436/81; 436/83; 436/166; 436/167; 436/168; 436/169; 422/58; 422/83; 55/270
[58] Field of Search ...................... 55/270, 429, 462, 55/465; 422/56, 58–60, 83–88; 436/77, 81, 83, 52, 166, 167–169

[56] References Cited

U.S. PATENT DOCUMENTS

| | | | |
|---|---|---|---|
| 1,711,742 | 5/1929 | Nordlander | 436/81 |
| 2,812,243 | 11/1957 | Goody | 422/87 |
| 3,868,222 | 2/1975 | Barringer | 55/270 X |
| 3,970,428 | 7/1976 | Barringer | 422/83 X |
| 4,485,665 | 12/1984 | Norman | 422/87 X |
| 4,752,447 | 6/1988 | Kimmel et al. | 422/56 |
| 4,829,007 | 5/1989 | Koslow | 436/80 |

OTHER PUBLICATIONS

L. T. Fairhall et al. *J. Am. Chem. Soc.* 1931, 53, 1321–1323.
S. S. Gurvits et al. *Chem. Abstr.* 1942, 36, 2226.
L. Silverman et al. *J. Ind. Hyg. Toxic,* 1943, 25, 185–188.
K. R. May *J. Sci Instru* 1945, 22, 187–195.
L. Silverman et al. *J. Ind. Hyg. Toxic,* 1946, 28, 107–111.
O. Tada *J. Sci. Labour* 1968, 44, 10–22.
P. Drinker et al. "Industrial Dust" 2nd. ed., McGraw–Hill Book Company, Inc.: New York, 1954, pp. 123–146 & 347–371.
L. S. Karol et al. *Chem. Abstr.* 1974, 81, 85528y.
A. A. Tikhomirova et al. *J. Anal. Chem. USSR* 1976, 31, 240–242.
P. R. Walsh et al. *Environ. Sci. Technol.* 1977, 11, 163–166.
Y. P. Grover *Anal. Chim. Acta* 1978, 101, 225–228.
S. E. Birnie et al. *Analyst* 1980, 105, 110–118.
D. Frahme et al. *Chem. Abstr.* 1983, 98, 221915c.

*Primary Examiner*—Jill Warden
*Assistant Examiner*—Arlen Soderquist
*Attorney, Agent, or Firm*—M. E. Lachman; M. W. Sales; W. K. Denson-Low

[57] ABSTRACT

An improved device for monitoring the presence of toxic metals in workplace air comprises a base and a removable top assembly. The top assembly includes a test substrate, such as filter paper, having a first surface and a second surface. The first surface is supported by the top assembly and the second surface has an area that is sensitized with at least one chemical reagent for producing a reaction with at least one toxic metal. The base has an air inlet, an air outlet, and a channel connecting the air inlet and the air outlet, thereby enabling air entering the monitor from the air inlet to directly contact the area of the second surface of the test substrate prior to exiting the monitor through the air outlet.

11 Claims, 1 Drawing Sheet

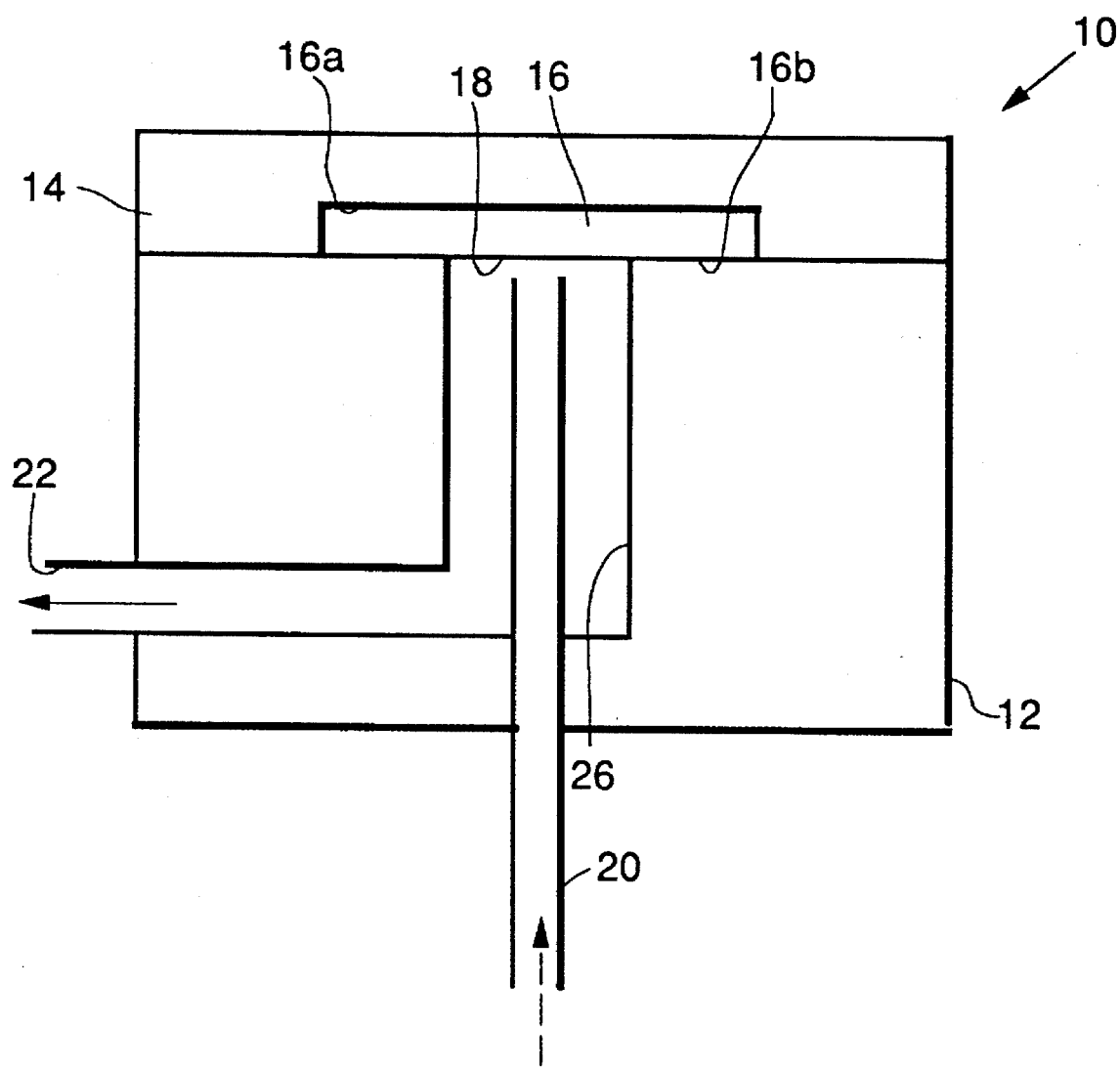

TIME AVERAGED TOXIC METALS MONITORING METHOD

BACKGROUND OF THE INVENTION

1. Field of the Invention

The present invention relates to an improved device for monitoring the presence of toxic metals in workplace air.

2. Description of Related Art

Toxic metals have a negative impact on human health. The term toxic metals is used herein to include hazardous, inorganic species, such as cadmium, lead, mercury, and arsenic, and their salts, such as oxides, chlorides, acetates, nitrates, perchlorates, and phosphates. The use of toxic metals in the workplace necessitates stringent precautions against accidental release. The Occupational Safety and Health Agency (OSHA) has recently reduced the permissible exposure limit of personnel to airborne cadmium particles to 5.0 micrograms/cubic meter and stipulated an action level for airborne cadmium particles at 2.5 micrograms/cubic meter. Corporations are now faced with a significant liability associated with the exposure of personnel to these materials.

At present, the most commonly used personnel monitors rely upon adsorbent or absorbent tubes and miniature air sampling pumps, followed by laboratory chemical analysis of compounds collected over long periods of time. Organizations that do not have in-house laboratories must often wait days for these analytical results. The detection limits of many of these monitors often lack the sensitivity required by OSHA and suffer from interferences that are difficult or impossible to resolve.

Prior personnel monitors for cadmium require the collection filter from a personnel air sampling pump to be sent to an off-site laboratory for analysis by skilled chemical technicians. Results of these tests are not available for several days. Personnel may experience multiple days of cadmium exposure before corrective action can be taken.

Thus, a need exists for a sensitive, quick response monitor for toxic metals such as those listed above, with detection limits that meet the new, lower OSHA exposure limits for toxic metals, to safeguard both workers and the environment.

SUMMARY OF THE INVENTION

In accordance with the present invention, an improved device is provided for monitoring the presence of toxic metals in workplace air. The device comprises:

(a) a monitor comprising a base and a removable top assembly;

(b) the removable top assembly having a test substrate with a first and a second surface, the first surface supported by the top assembly and the second surface having an area sensitized with at least one chemical reagent for producing a reaction with at least one toxic metal; and (c) the base having an air inlet, an air outlet, and a channel connecting the air inlet and the air outlet, thereby enabling air entering the monitor from the air inlet to directly contact the sensitized area of the second surface of the test substrate prior to exiting the monitor through the air outlet.

The present invention provides a device for monitoring the time averaged concentration of toxic metals such as cadmium, lead, mercury, and arsenic in workplace air. The device of the present invention will detect when workers have been exposed to concentrations of toxic metals greater than that allowed by OSHA requirements. Rather than waiting several days for off-site testing, the test results from the present invention can be quickly evaluated by the worker, plant safety officer, or automated particle counter immediately at the end of a work shift, or other designated time period. If high levels of toxic metals such as cadmium, lead, mercury, and arsenic are detected, immediate action can be taken to identify the source and apply remedial action. If necessary, the worker can be treated for toxic metal overdose immediately.

BRIEF DESCRIPTION OF THE DRAWINGS

The sole FIGURE depicts a cross-sectional view of the time averaged toxic metals monitor of the present invention.

DESCRIPTION OF THE PREFERRED EMBODIMENTS

The present invention comprises an improved device for monitoring the presence of toxic metals in workplace air. The monitoring device comprises a monitor 10 with a base 12 and a removable top assembly 14. The top assembly 14 includes a test substrate 16, such as a filter paper, having a first surface 16a and a second surface 16b. The first surface 16a is supported by the top assembly 14 and the second surface 16b has an area 18 that is sensitized with at least one chemical reagent for producing a reaction with at least one toxic metal.

The base 12 has an air inlet 20, an air outlet 22, and a channel 26 connecting the air inlet 20 and the air outlet 22. The air inlet 20 enables air entering the monitor 10 to directly contact the sensitized area 18 of the second surface 16b of the test substrate 16 prior to exiting the monitor through channel 26 and out the air outlet 22.

The test substrate 16 comprises filter paper, as described above, such as glass filter paper Grade 111, Cat. No. F2330-42, available from American Scientific Products, McCaw Park, Ill. Alternatively, substrates 16 such as gels or solid polymer electrolytes may be used in place of the filter paper.

The requirements are that the substrate 16 must be sticky to trap the particles and must be able to contain the necessary reagents. Use of gels and polymer electrolytes requires impinger technology, that is, directing the incoming air stream from air inlet 20 against the test substrate 16 at a right angle (normal to the plane of the substrate). Dust particles will impact on the substrate 16, while the air continues on through the air outlet 22. To ensure that the particles are trapped and not blown away, the distance between the end of the air inlet 20 and the substrate 16 should be smaller than the inside diameter of the air inlet 20. Filter paper can also be used in the impinger mode, or may be installed such that the air stream passes through the paper.

Although the following description of the present invention covers the detection of a particular toxic metal, cadmium, the present invention is not limited to any one toxic material. As previously defined the term toxic metals is used herein to include but is not limited to hazardous, inorganic species, such as cadmium, lead, mercury, and arsenic, and their salts, such as oxides, chlorides, acetates, nitrates, perchlorates, and phosphates.

In a preferred embodiment, ambient air, sampled from a point near the worker's mouth and nose, is drawn into the monitor using a commercially available personnel air sampling pump. Cadmium, cadmium oxide, and cadmium salt particles contained in the air are collected on the test substrate 16. Reagents (not shown) used to sensitize the test substrate 16 to thereby form the sensitized area 18 dissolve the particles to form cadmium ions. The cadmium ions are then reacted with additional reagents to form brightly colored spots. The development of the colored spots may occur immediately after capture or may require separate addition of a reagent to develop the colors prior to analysis of the presence of toxic metals on the test substrate. At the end of a work shift or other designated time period, the test substrate 16 is removed from the monitor 10 and examined under a microscope. The colors produced will be unique to cadmium, making interpretation possible by the user with minimal training. A simple count of the number of spots and a knowledge of the designated time period for sampling workplace air will reveal the time averaged concentration of cadmium. For example, assume that 1 liter of air is sampled over an eight hour period, with a concentration of 10 μg/m$^3$ and the cadmium particles average 10 micrometers in diameter. If the sensitized substrate area is 100 cm$^2$, then each square millimeter of substrate will contain 26 colored spots. If 65 colored spots are found, then the cadmium concentration has reached the action limit of 2.5 μg/m$^3$.

Maintenance of the monitor 10 of the present invention includes the daily replacement of the test substrate 16 with a new test substrate having a surface 16b freshly sensitized with an appropriate reagent.

The monitor 10 can operate with a variety of reagents, each of which can produce uniquely-colored spots in the presence of cadmium. Different reagent systems will be required to detect specific toxic metals. Some reagent systems can be used to detect pairs of toxic metals.

In the case of detecting cadmium, a first, solubilizing reagent is applied to the second surface 16b of the test substrate 16 to form the sensitized area 18. Then, a second, precipitating reagent is used to develop the sensitized area 18. For example, the solubilizing reagent may comprise sulfuric acid, e.g., 1 to 50%, and the precipitating reagent may comprise a mixture of sodium hydroxide (e.g., 1 Normal) and sodium sulfide (e.g., 1%). Or, the solubilizing reagent may comprise sulfuric acid (e.g., 1%) and an aqueous solution of thioacetamide (e.g., 10%) and the precipitating reagent may comprise an aqueous solution of sodium hydroxide (e.g., 1 Normal). Or, a combined solubilizing and precipitating solution may be employed, comprising a mixture of 1 to 30% hydroponic acid and 0.1 to 1% ferrous dipyridyl iodide, without requiring an additional reagent. Or, the solubilizing reagent may comprise an aqueous solution of 10 to 30 grams/liter sodium bitartrate, 10 to 50 grams/liter tartaric acid, and 1 to 10 grams/liter sodium sulfide and the precipitating reagent may comprise a 0.5 to 5 grams/liter sodium rhodizonate solution. This last reaction scheme can be used to detect both lead and cadmium. Under a microscope, the lead appears as scarlet spots, while the cadmium appears as yellow spots. Most other metals appear as black spots.

In many instances, visual inspection under a microscope is sufficient to determine the number of spots produced by the chemical reaction, using visible light. In some instances, depending on the reagent system selected, the spots produced may fluoresce under ultraviolet light, or may reflect ultraviolet light. Thus, it may be possible to distinguish between metals which are not differentiated under visible light.

The preferred chemistry depends on the type of metals being monitored. The selected chemical system should produce spots which are brightly and uniquely colored to aid in differentiation, be simple to use, stable with time, and pose minimal chemical exposure risk to operator. Tests for any of the toxic metals may be devised, based on the teachings herein, by one skilled in the art of analytical chemistry, without undue experimentation. Specific examples of these reagent systems are described below.

EXAMPLES

Example 1

A reagent-impregnated glass fiber filter paper (grade 111, Cat. #F2330-42 from American Scientific Products, McCaw Park, Ill.) was sensitized by immersion in 1% H$_2$SO$_4$ solution. The paper was then allowed to dry in air, until the acid equilibrated with atmospheric moisture (about 40 wt %).

Several particles of cadmium metal and cadmium oxide were then added to the paper and allowed to react for 30 minutes.

After exposure, the paper was developed by spraying on a mixture of 1N NaOH solution and 1% Na$_2$S.

After developing, the paper was examined under a microscope. The particles were surrounded by circular spots of bright yellow cadmium sulfide. The yellow spots were about 10 times the diameter of the original cadmium metal particles and about 20 times the diameter of the cadmium oxide particles. This expansion simplifies the ability to detect the particles. The larger cadmium particles were about 10 micrometers in diameter and yielded spots about 100 micrometers in diameter. These spots were easily visible under about 10×. Spots generated from 0.1 micrometer particles were about 1 micrometer in diameter and were easily visible under about 70×. Higher microscope powers could be used to detect particles that are even smaller.

Following is a description of the chemistry occurring on the substrate:

The cadmium and cadmium oxide must first be converted into a soluble form. In this case, solubilization was achieved with sulfuric acid. If acid is used, it must be capable of forming a water-soluble cadmium salt. The acid ideally must also be able to retain moisture in the presence of a large volume of air. A strong solution of sulfuric acid satisfies both of these requirements. Other non-volatile hygroscopic acids such as phosphoric or lactic acid can also be used. Non-acidic solubilizing agents such as ammonium nitrate can also be used.

In the case of sulfuric acid, metallic cadmium particles react according to the following equation:

$$Cd + H_2SO_4 \rightarrow Cd^{2+} + SO_4^{2-} + H_2.$$

Cadmium oxide reacts in a similar way:

$$CdO + H_2SO_4 \rightarrow Cd^{2+} + SO_4^{2-} + H_2O.$$

Cadmium salts simply dissolve in the acidic mixture.

After the substrate filter has been exposed to air for the desired time interval, the filter paper is developed by spraying with or immersing the paper in a mixture of sodium hydroxide and sodium sulfide. The sodium hydroxide neutralizes any excess acid, thus preventing the evolution of hydrogen sulfide. Any cadmium ions in solution then precipitate out, and are developed as bright yellow spots of cadmium sulfide:

$Cd^{2+}+Na_2S \rightarrow CdS+2Na^+$.

These spots are easily visible under a microscope. The sensitivity of the method will depend on the power of the microscope. Higher powers will be needed for low concentrations of cadmium, especially for finer sized particulates.

Metals other than cadmium will result in colors other than bright yellow, and hence will not interfere with interpretation of the test. Metals that are likely to be present in refurbishing shops will likely include aluminum, iron, copper, and nickel. These metals will show up with the following colors:

| | |
|---|---|
| aluminum | white |
| iron | dark brown |
| copper | black |
| nickel | black. |

As a consequence of these substantially different colors, a skilled technician will not be needed to interpret the results. The test results may be masked by an overwhelming amount of these other metals. However, since most of these metals are at least somewhat toxic, such a response is an indication that exposure reductions are needed.

Example 2

This example is a variation of the sulfide formation given in Example 1.

A reagent-impregnated glass fiber filter paper, as described in Example 1, was sensitized as follows:

(1) The paper was immersed in 1% $H_2SO_4$ solution and then dried in air.

(2) Several drops of 10% thioacetamide solution were added to the paper, which was then dried in air. Thioacetamide provides hydrogen sulfide as it hydrolyzes according to the following reaction:

$CH_3CSNH_2+H_2O \rightarrow CH_3CONH_2+H_2S$.

Several particles of cadmium metal were then added to the paper and allowed to react for 15 minutes.

After exposure, the spots were developed by spraying the paper with 1N NaOH solution. The NaOH reacts to provide sodium sulfide:

$NaOH+H_2S \rightarrow Na_2S$.

The $Na_2S$ then reacts with cadmium ion to produce the yellow spots as in Example 1.

After development, the paper was examined under a microscope. As in Example 1, the particles were surrounded by circular spots of bright yellow cadmium sulfide which were easily visible under 10× to 70×.

Example 3

The following reagent system may be used to detect cadmium. Cadmium and cadmium compounds are dissolved in hydroiodic acid (HI) to yield a complex as follows:

$Cd+4HI \rightarrow CdI_4^{2-}+2H^++H_2$.

The tetraiodocadmium complex is then reacted with ferrous dipyridyl iodide to produce a red-violet precipitate.

$CdI_4^{2-}+Fe(a,a'-dip)_3I_2 \rightarrow [Fe((a,a'-dip)_3]\cdot[CdI_4]+2I^-$.

Since this reaction can be conducted in an acidic environment, both the hydroiodic acid and ferrous dipyridyl iodide can be supplied in the test substrate. A separate developing step is not necessary prior to analysis.

Example 4

The following reagent system may be used to detect lead and lead based oxides and salts in addition to detecting cadmium. A test substrate is sensitized by soaking a commercially available filter paper in a solution of the following reagent:

sodium bitartrate (19 grams/liter);

tartaric acid (15 grams/liter); and sodium sulfide (10 grams/liter).

Dust particles are collected using a personnel air sampling pump to sample workplace air and then colored spots are developed by spraying a sodium rhodizonate (2 grams/liter) reagent on the test substrate. When examined under a microscope, the lead appears as scarlet spots and the cadmium appears as yellow spots, as described in Example 1. In this scheme, most other metals will appear as black spots.

Thus, there has been disclosed an improved method for monitoring the presence of toxic metals in workplace air. It will be readily apparent to those of ordinary skill in this art that various changes and modifications of an obvious nature may be made, and all such changes and modifications are considered to fall within the scope of the invention, as defined by the appended claims.

What is claimed is:

1. An improved method for monitoring workplace air, comprising;

(a) providing a monitor comprising a base and a removable top assembly, (1) said top assembly comprising a test substrate with a first and a second surface, said first surface supported by said top assembly, and (2) said base having an air inlet, an air outlet, and a channel connecting said air inlet and said air outlet, thereby enabling air entering said monitor from said air inlet to directly contact a sensitized area of said second surface of said test substrate prior to exiting said monitor through said air outlet;

(b) sensitizing said second surface of said test substrate with at least one chemical solution for solubilizing at least one toxic metal;

(c) pumping a volume of said workplace air through said air inlet of said monitor for a designated time period, said volume of air coming in direct contact with said sensitized area of said test substrate to solubilize said at least one toxic metal and then exiting said monitor through said air outlet;

(d) removing said test substrate from said monitor and exposing said second surface of said test substrate to a precipitating solution for developing said toxic metal to form colored spots;

(e) examining said second surface of said test substrate to obtain a count of said colored spots on said test substrate; and (f) obtaining a time averaged concentration of said toxic metal from said count of said colored spots on said test substrate and said designated time period.

2. The method of claim 1 wherein said toxic metal is selected from the group consisting of cadmium, lead, mercury, and arsenic.

3. The method of claim 1 wherein said test substrate comprises a member selected from the group consisting of filter paper, a gel, and a solid polymer electrolyte.

4. The method of claim 1 wherein said at least one solubilizing solution comprises a sulfuric acid solution having a concentration in the range of 1 to 50% and wherein said developing solution comprises a mixture of 1 Normal sodium hydroxide and 1% sodium sulfide.

5. The method of claim 1 wherein said test substrate comprises a glass fiber filter paper, wherein said at least one chemical solution comprises a first, solubilizing solution comprising (a) a 1% sulfuric acid solution and (b) a 10% thioacetamide solution and a second, precipitating solution comprising a 1 Normal solution of sodium hydroxide.

6. The method of claim 1 wherein said test substrate comprises a glass fiber filter paper and wherein said first, solubilizing solution comprises a mixture of 1 to 30% hydroiodic acid and 0.1 to 1% ferrous dipyridyl iodide.

7. The method of claim 1 wherein said test substrate comprises a filter paper, said first solubilizing solution comprises a mixture of about 10 to 30 grams/liter of sodium bitartrate, 10 to 50 grams/liter of tartaric acid, and 1 to 10 grams/liter of sodium sulfide, and said second, precipitating solution comprises about 0.5 to 5 grams/liter of sodium rhodizonate.

8. The method of claim 7 wherein said toxic metals detected include cadmium and lead.

9. The method of claim 1 wherein said second surface of said test substrate is examined at microscopic magnification ranging from about 10× to 70× using either visible illumination or ultraviolet illumination.

10. An improved method for monitoring workplace air, comprising;

(a) providing a monitor comprising a base and a removable top assembly, (1) said top assembly comprising a test substrate with a first and a second surface, said first surface supported by said top assembly, and (2) said base having an air inlet, an air outlet, and a channel connecting said air inlet and said air outlet, thereby enabling air entering said monitor from said air inlet to directly contact a sensitized area of said second surface of said test substrate prior to exiting said monitor through said air outlet;

(b) sensitizing said second surface of said test substrate with at least one chemical solution for solubilizing at least one toxic metal and at least one chemical solution for precipitating a product of said solubilized toxic metal to produce colored spots;

(c) pumping a volume of said workplace air through said air inlet of said monitor for a designated time period, said volume of air coming in direct contact with said sensitized area of said test substrate to solubilize and subsequently precipitate said at least one toxic metal and then exiting said monitor through said air outlet;

(d) removing said test substrate from said monitor;

(e) examining said second surface of said test substrate to obtain a count of said colored spots on said test substrate; and (f) obtaining a time averaged concentration of said toxic metal from said count of said colored spots on said test substrate and said designated time period.

11. The method of claim 10 wherein said solubilizing solution comprises hydroiodic acid and said chemical solution for precipitating comprises ferrous dipyridyl iodide.

* * * * *